United States Patent
Yamada et al.

(10) Patent No.: US 12,239,598 B2
(45) Date of Patent: Mar. 4, 2025

(54) WALKING ASSISTANCE DEVICE

(71) Applicant: YAMADA Co., Ltd., Hamamatsu (JP)

(72) Inventors: Yoshihiro Yamada, Hamamatsu (JP); Etsuyo Yamada, Hamamatsu (JP)

(73) Assignee: YAMADA CO., LTD, Shizuoka (JP)

( * ) Notice: Subject to any disclaimer, the term of this patent is extended or adjusted under 35 U.S.C. 154(b) by 478 days.

(21) Appl. No.: 17/603,029

(22) PCT Filed: Aug. 19, 2019

(86) PCT No.: PCT/JP2019/032311
§ 371 (c)(1),
(2) Date: Oct. 12, 2021

(87) PCT Pub. No.: WO2021/033243
PCT Pub. Date: Feb. 25, 2021

(65) Prior Publication Data
US 2022/0192911 A1    Jun. 23, 2022

(51) Int. Cl.
*A61H 3/00* (2006.01)
*A61H 1/02* (2006.01)

(52) U.S. Cl.
CPC .............. *A61H 3/00* (2013.01); *A61H 1/024* (2013.01); *A61H 1/0266* (2013.01);
(Continued)

(58) Field of Classification Search
CPC .... A61H 3/00; A61H 3/008; A61H 2003/007; A61H 1/0237; A61H 1/024;
(Continued)

(56) References Cited

U.S. PATENT DOCUMENTS

| | | | |
|---|---|---|---|
| 1,308,675 A | * | 7/1919 | Kelley .................. B25J 9/0006 601/35 |
| 6,428,495 B1 | * | 8/2002 | Lynott .................. A61F 5/3715 602/23 |

(Continued)

FOREIGN PATENT DOCUMENTS

| | | |
|---|---|---|
| CN | 106377386 A | 2/2017 |
| DE | 202018002263 U1 | 5/2018 |

(Continued)

OTHER PUBLICATIONS

Extended European Search Report dated Mar. 16, 2023 for European Appl. No. 19942504.2.

(Continued)

*Primary Examiner* — Joseph D. Boecker
*Assistant Examiner* — Brian T Khong
(74) *Attorney, Agent, or Firm* — Ohlandt, Greeley and Perle, L.L.P.

(57) ABSTRACT

A walking assistance device includes a belt-shaped lumbar region fixture, a first elastic string-like member, and a second elastic string-like member, wherein each of the first elastic string-like member and the second elastic string-like member is configured to be bifurcated near a knee of a leg, and the bifurcated parts of the first elastic string-like member and the second elastic string-like member are configured to be directly bound to each other at positions of an outer knee joint fissure gap and an inner knee joint fissure gap.

14 Claims, 11 Drawing Sheets

(52) U.S. Cl.
CPC .. *A61H 2001/027* (2013.01); *A61H 2003/001* (2013.01); *A61H 2003/007* (2013.01); *A61H 2201/1253* (2013.01); *A61H 2201/1623* (2013.01); *A61H 2201/164* (2013.01); *A61H 2201/165* (2013.01)

(58) Field of Classification Search
CPC ................ A61H 1/0244; A61H 1/0262; A61H 2201/1253; A61H 2201/1261; A61H 2201/1269; A61H 2201/1642; A61H 2201/1652; A63B 21/4001; A63B 21/4009; A63B 21/4011; A63B 21/4013; A63B 21/4015; A63B 21/4025; A63B 21/055; A63B 21/0552; A63B 21/0555; A63B 21/0557; A61F 2005/0179; A41D 31/18; B25J 9/0006
See application file for complete search history.

(56) References Cited

U.S. PATENT DOCUMENTS

| | | | |
|---|---|---|---|
| 2007/0004570 A1 | 1/2007 | Afanasenko et al. | |
| 2013/0190147 A1* | 7/2013 | Luo | A63B 21/4025 482/122 |
| 2015/0190669 A1* | 7/2015 | Matsuura | A63B 21/4017 482/8 |
| 2016/0107309 A1* | 4/2016 | Walsh | A63B 21/0054 248/550 |
| 2017/0105862 A1 | 4/2017 | Griggs | |
| 2018/0078443 A1* | 3/2018 | Aslani | A61H 3/00 |

FOREIGN PATENT DOCUMENTS

| | | |
|---|---|---|
| JP | 54-077593 | 6/1979 |
| JP | 7-501963 | 3/1995 |
| JP | 3038150 | 6/1997 |
| JP | 3119871 | 3/2006 |
| JP | 2018-201846 | 12/2018 |
| JP | 2019141312 A | 8/2019 |
| WO | 2006/110034 | 10/2006 |
| WO | 2006110034 A2 | 10/2006 |
| WO | 2015187961 A1 | 12/2015 |

OTHER PUBLICATIONS

International Search Report dated Oct. 29, 2019 in corresponding International PCT Patent Application No. PCT/JP2019/032311, 2 pgs.

India Office Action dated Mar. 31, 2022 for Japanese Appl. No. 20117045287.

Japanese Office Action dated Nov. 15, 2021 for Japanese Appl. No. 2018-028348.

* cited by examiner

WALKING ASSISTANCE DEVICE

TECHNICAL FIELD

The present disclosure relates to a walking assistance device for assisting walking.

BACKGROUND ART

Various walking assistance devices for assisting walking by an aged person and a disabled person having difficulty in walking have been conventionally proposed. For example, a wearable device for walking assistance in Patent Literature 1 includes a cloth interwoven with rubber made of an appropriately elastic material or object, one end of the cloth being fixed to a belt at the waist, the cloth covering a knee when the knee joint is bent and stretched, and the other end being fixed to the position of an ankle; and the device also includes movement prevention bands provided in an upper part of the knee and an upper position of a calf in such a way as not to cover a dimple on the rear side of the knee, and when the knee joint is bent, the cloth having a long length stretches while covering the knee. Accordingly, the stretching force improves a distance-walking ability by the device being in constant wear without a feeling of tightening, the wear causing elasticity derived from a contractile force caused when the knee joint is straightened to contribute to an assisting force against decrease in an active force of a user.

Further, for example, a safe walking assistance device in Patent Literature 2 including two pieces of elastic with high elasticity is worn by each piece of elastic being fixed by a fastener attachable to and detachable from a toe, the fastener being provided at an end of the elastic, the pieces of elastic being integrally fixed by a fixing band provided in an ankle region and being fixed by a fixing band provided in a knee region while splitting left and right, and an upper part of the pieces of elastic being pulled up to a lumbar region and being secured in the lumbar region.

CITATION LIST

Patent Literature

Patent Literature 1: Japanese Utility Model Registration No. 3038150
Patent Literature 2: Japanese Utility Model Registration No. 3119871

SUMMARY OF INVENTION

Technical Problem

However, none of the conventional walking assistance devices can lift the sole of a foot and cannot provide support for walking up a stairway or a hill easily.

The present disclosure has been made in view of such circumstances and is for providing a walking assistance device that can provide support for facilitating walking while lifting the sole of a foot.

Solution to Problem

A walking assistance device according to claim 1 includes: a belt-shaped lumbar region fixture wound around a lumbar region; a first elastic string-like member an upper part of which is fixed to the lumbar region fixture at a position of an anterior superior iliac spine and a lower part of which extends in an instep direction and is hooked to a toe region of a sole; and a second elastic string-like member an upper part of which is fixed to the lumbar region fixture above a position of an ischial tuberosity and a lower part of which extends in an ankle direction and is hooked to a heel region of the sole, wherein each of the first elastic string-like member and the second elastic string-like member is bifurcated near a knee of a leg, and the bifurcated parts of the first elastic string-like member and the second elastic string-like member are bound to each other at positions of an outer knee joint fissure gap and an inner knee joint fissure gap.

In a walking assistance device according to claim 2, the first elastic string-like member is bifurcated between a position above a kneecap and a position of a tibial tuberosity.

In a walking assistance device according to claim 3, the second elastic string-like member is bifurcated between a position in a lower part of a thigh and a position in an upper part of a lower leg.

In a walking assistance device according to claim 4, the first elastic string-like member and the second elastic string-like member are fixed to an ankle by an ankle binding fixture.

A walking assistance device according to claim 5, includes: a belt-shaped lumbar region fixture wound around a lumbar region; a first elastic string-like member an upper part of which is fixed to the lumbar region fixture at left and right positions with an anterior superior iliac spine in between and a lower part of which extends in an instep direction and is hooked to a toe region of a sole; and a second elastic string-like member an upper part of which is fixed to the lumbar region fixture above left and right positions with an ischial tuberosity in between and a lower part of which extends in an ankle direction and is hooked to a heel region of the sole, wherein each of the first elastic string-like member and the second elastic string-like member descends from a lumbar region fixture in two lines, and the bifurcated parts of the first elastic string-like member and the second elastic string-like member are bound to each other at positions of an outer knee joint fissure gap and an inner knee joint fissure gap.

In a walking assistance device according to claim 6, the first elastic string-like member descends from the lumbar region fixture in two lines, and the lines are bound together at a position above a kneecap and a position of a tibial tuberosity.

In a walking assistance device according to claim 7, the second elastic string-like member descends from the lumbar region fixture in two lines, and the lines are bound together at a position in a lower part of a thigh and a position in an upper part of a lower leg.

In a walking assistance device according to claim 8, the first elastic string-like member and the second elastic string-like member are fixed to an ankle by an ankle binding fixture.

Advantageous Effects of Invention

A walking assistance device according to the present disclosure can provide support for facilitating walking while lifting the sole of a foot.

DESCRIPTION OF EMBODIMENTS

A walking assistance device according to the present disclosure is for assisting walking by an aged person or a disabled person having difficulty in walking. Further, the walking assistance device according to the present disclosure may not only be used for assisting daily walking but may also be used for walking exercises. Furthermore, the walking assistance device according to the present disclosure can be used in every aspect of walking such as walking in sports and leisure, and mountain climbing, and a wide range of actions using legs such as jogging without being limited to walking.

A basic structure of the walking assistance device includes a belt-shaped lumbar region fixture wound around a lumbar region, a first elastic string-like member, and a second elastic string-like member. The lumbar region fixture is not limited by the shape or the like as long as the fixture can fix the first elastic string-like member and the second elastic string-like member to be described later at predetermined positions of the waist and may be a commercially available belt or the like. While the walking assistance device can be used on either of left and right legs, embodiments will be described in the case of use on the right leg.

Each of the first elastic string-like member and the second elastic string-like member is a string-like member having predetermined elasticity, such as a piece of elastic. Further, each of the first elastic string-like member and the second elastic string-like member is not limited by the shape and may be band-shaped or tubular as long as the member has the predetermined elasticity and a long length; and the material of the member may be natural rubber, leather, or an elastic resin material. Further, a large thickness (width) is not so suitable for each of the first elastic string-like member and the second elastic string-like member since the members are bound together as will be described later, and a diameter (width) of 3 mm to 20 mm is easy to use. For example, "Thera Tube (registered trademark)" from D&M Co., Ltd. may be used as the first elastic string-like member and the second elastic string-like member.

As for resistance (that is, elasticity) of each of the first elastic string-like member and the second elastic string-like member, resistance of 0.8 kg to 2.8 kg when each of the first elastic string-like member and the second elastic string-like member with a length of 600 mm is extended by 200 mm is desirable in view of supporting walking.

It is desirable to appropriately select each of the first elastic string-like member and the second elastic string-like member to be used out of members with varying resistance, based on the weight and symptom of a user.

In a basic form of the walking assistance device according to the present disclosure, the first elastic string-like member is provided on the front side of a leg, an upper part of the member is fixed to the lumbar region fixture and a lower part of the member extends in an instep direction and is hooked to a toe region of a sole; and the second elastic string-like member is provided on the rear side of the leg, an upper part of the member is fixed to the lumbar region fixture, and a lower part of the member extends in an ankle direction and is hooked to a heel region of the sole. Then, in the form, each of the first elastic string-like member and the second elastic string-like member is bifurcated near the knee of the leg, and the bifurcated parts of the first elastic string-like member and the bifurcated parts of the second elastic string-like member are bound to each other at positions of an outer joint gap and an inner joint gap.

The walking assistance device with such a form can provide support for facilitating walking while lifting the sole of a foot.

Embodiment 1

Figure 1:
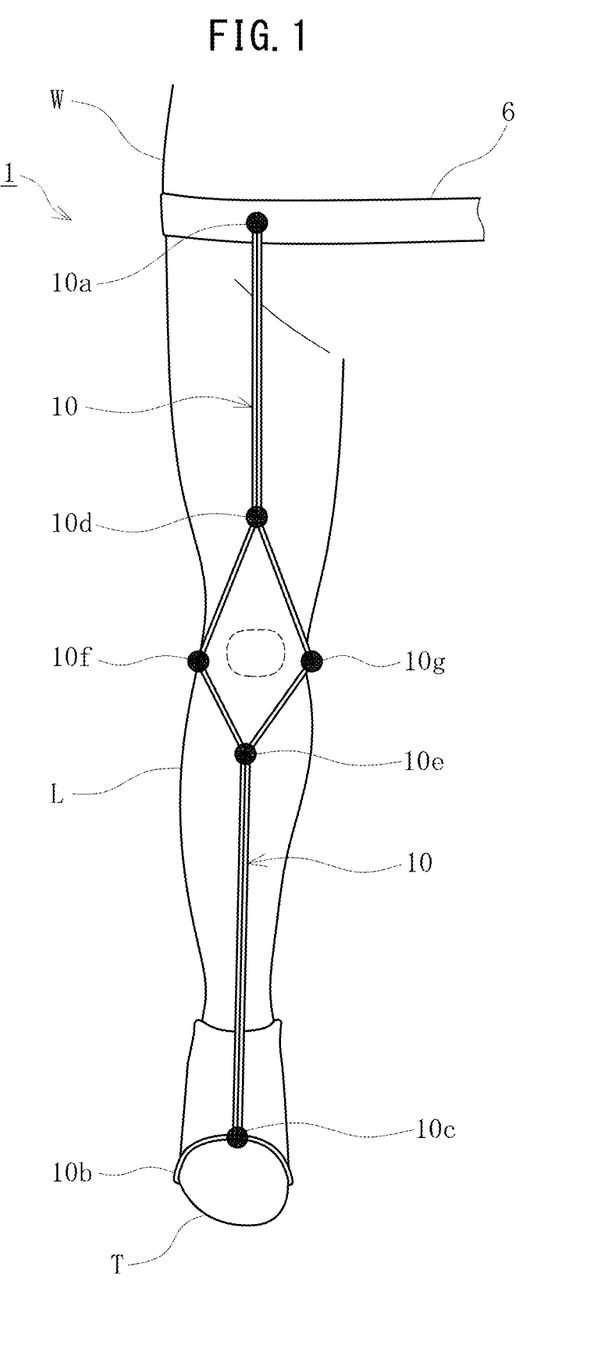
FIG. 1 is a diagram illustrating the front of a walking assistance device according to Embodiment 1 of the present disclosure.
Figure 2:
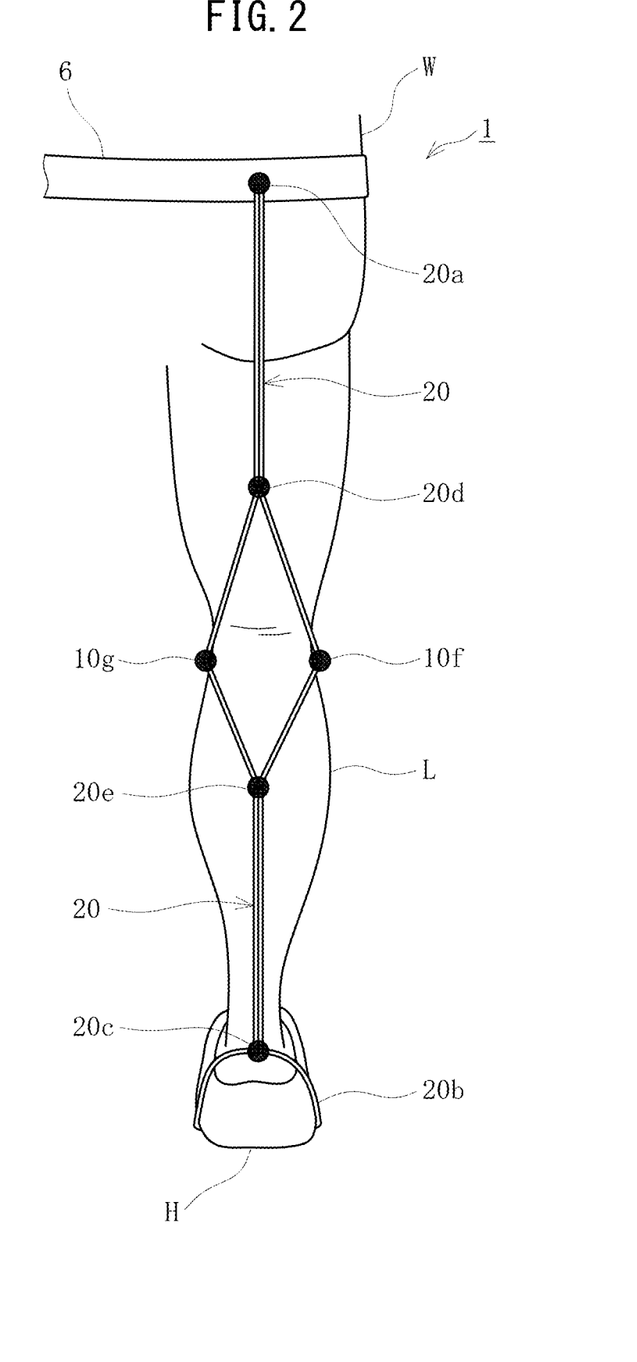
FIG. 2 is a diagram illustrating the rear of the walking assistance device according to Embodiment 1 of the present disclosure.
Figure 3:
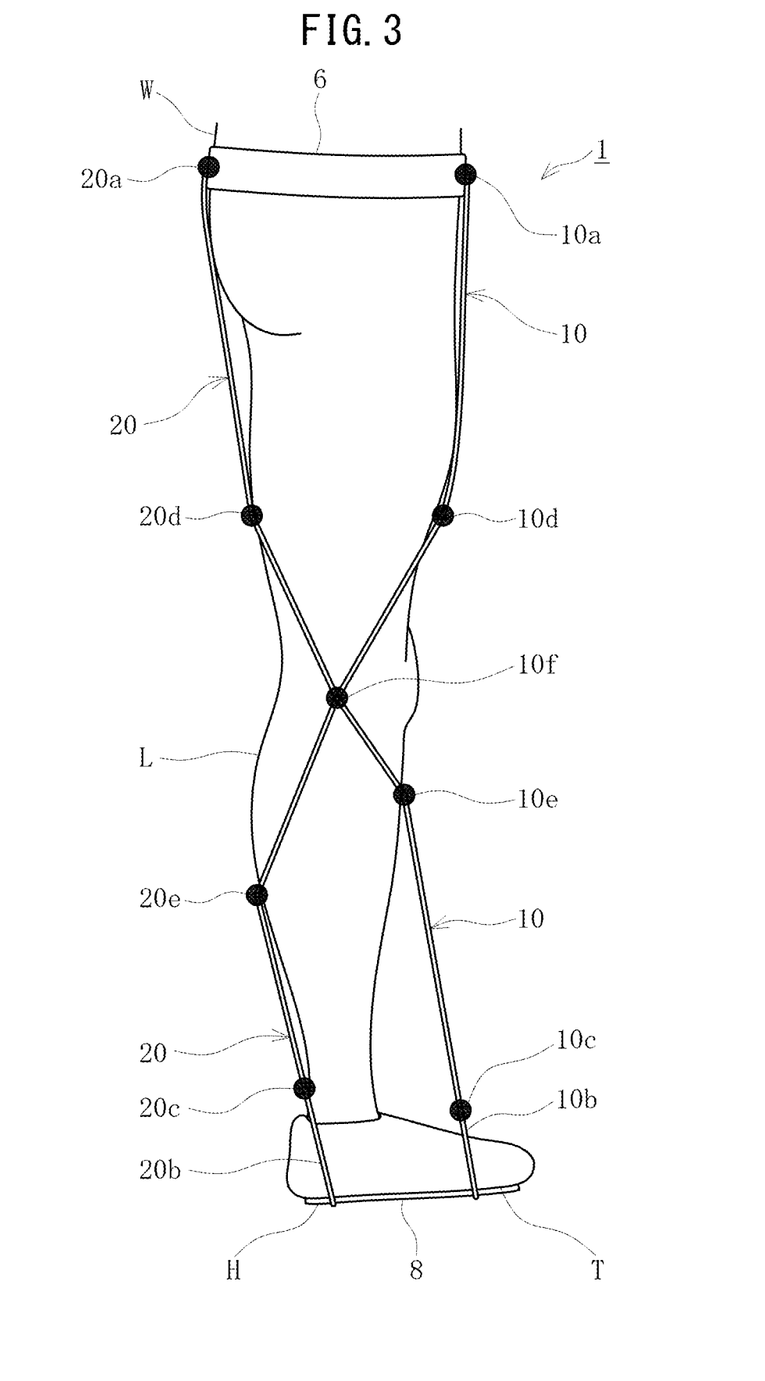
FIG. 3 is a diagram illustrating the left side of the walking assistance device according to Embodiment 1 of the present disclosure.
Figure 4:
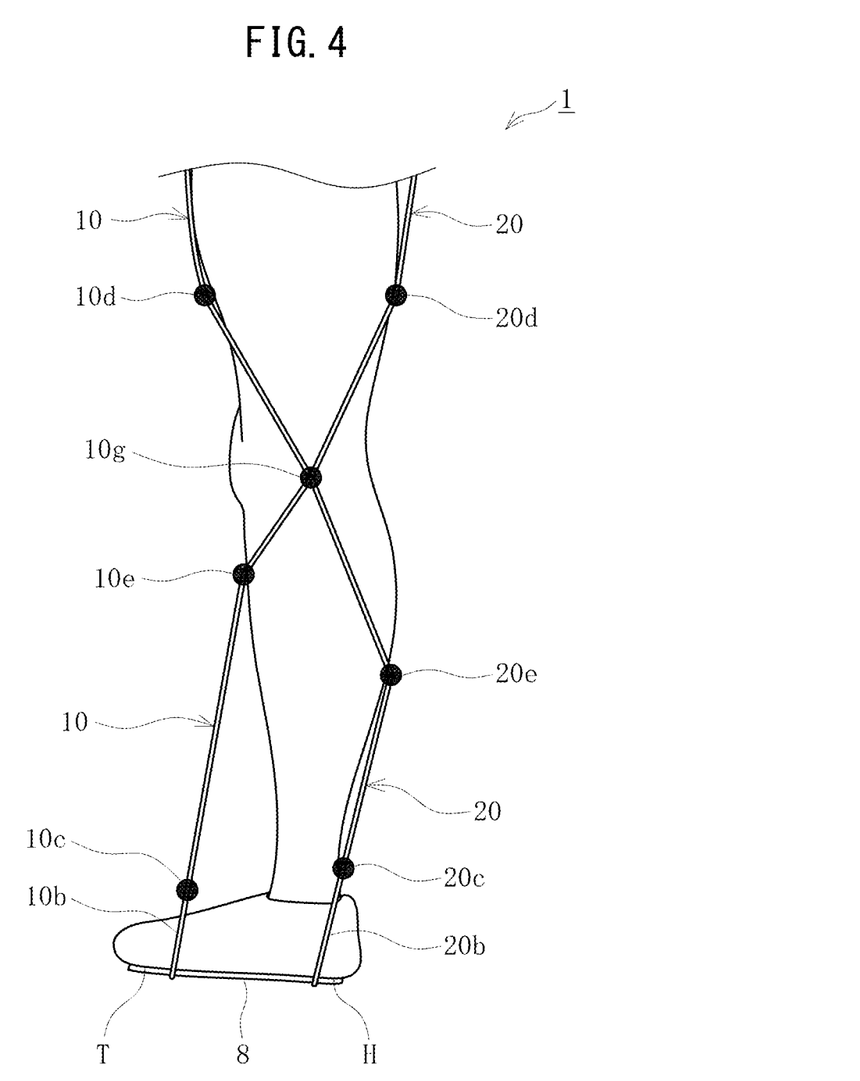
FIG. 4 is a diagram illustrating the right side of the walking assistance device according to Embodiment 1 of the present disclosure.

A walking assistance device according to Embodiment 1 will be described below by using FIG. 1 to FIG. 4. FIG. 1 is a diagram illustrating the front of the walking assistance device according to Embodiment 1 of the present disclosure. FIG. 2 is a diagram illustrating the rear of the walking assistance device according to Embodiment 1 of the present disclosure. FIG. 3 is a diagram illustrating the left side of the walking assistance device according to Embodiment 1 of the present disclosure. FIG. 4 is a diagram illustrating the right side of the walking assistance device according to Embodiment 1 of the present disclosure.

In a basic form of a first elastic string-like member 10 in the walking assistance device 1 according to the present embodiment, the first elastic string-like member 10 is bifurcated partway, a line of an upper part 10a is fixed to a lumbar region fixture 6 at the position of an anterior superior iliac spine, and a line of a lower part 10b extends in an instep direction of a leg L and is hooked to a toe region T of a sole. The first elastic string-like member 10 in the walking assistance device 1 may take a form of a single member being bifurcated partway, a form of doubling a single member and making part of the doubled member a single line by overlapping, or a form of two members being bound together partway and is not limited by the form of the member. The first elastic string-like member 10 will be described in the form of doubling a single member and making part of the doubled member a single line by overlapping in the following description.

Specifically, the upper part 10a of the first elastic string-like member 10 is fixed to the lumbar region fixture 6 at the position of the anterior superior iliac spine. Then, the first elastic string-like member 10 is bifurcated partway between a position above a kneecap and the position of a tibial tuberosity. The lower part 10b of the first elastic string-like member 10 extending to a toe in a downward direction becomes annular at a lower part binding part 10c and is hooked to the toe region T of the sole of the leg L.

Further, in a basic form of a second elastic string-like member 20 in the walking assistance device 1 according to the present embodiment, the second elastic string-like member 20 is bifurcated partway, an upper part of a line of an upper part 20a is fixed to the lumbar region fixture 6 above the position of an ischial tuberosity, and a line of a lower part 20b extends in an ankle direction of the leg L and is hooked to a heel region H of the sole. The second elastic string-like member 20 in the walking assistance device 1 may take a form of a single member being bifurcated partway, a form of doubling a single member and making part of the doubled member a single line by overlapping, or a form of two members being bound together partway and is not limited by the form of the member. The second elastic string-like member 20 will be described in the form of doubling a single member and making part of the doubled member a single line by overlapping in the following description.

Specifically, the upper part 20a of the second elastic string-like member 20 is fixed to the lumbar region fixture 6 above the position of the ischial tuberosity. Then, the second elastic string-like member 20 is bifurcated partway between a position in a lower part of a thigh and a position in an upper part of a lower leg. The lower part 20b of the second elastic string-like member 20 extending to a heel in the downward direction becomes annular at a lower part binding part 20c and is hooked to the heel region H of the sole of the leg L.

While the first elastic string-like member 10 and the second elastic string-like member 20 may be directly stretched to the sole of the leg L, a thin-plate-shaped sole member 8 may be provided between the sole, and the first elastic string-like member 10 and the second elastic string-like member 20. Use of the sole member 8 can provide an effect of lifting the entire sole.

Further, in the walking assistance device 1, the first elastic string-like member 10 and the second elastic string-like member 20 bind the bifurcated parts of the first elastic string-like member 10 and the second elastic string-like member 20 together at an outer knee joint fissure gap binding part 10f being the position of an outer knee joint fissure gap and an inner knee joint fissure gap binding part 10g being the position of an inner knee joint fissure gap.

In the form of the first elastic string-like member 10 in the walking assistance device 1 being bifurcated between the position above the kneecap and the position of the tibial tuberosity, the two lines of the first elastic string-like member 10 are bound together at an upper kneecap binding part 10d being the position above the kneecap and a tibial tuberosity binding part 10e being the position of the tibial tuberosity. Binding at the position above the kneecap and the position of the tibial tuberosity further facilitates walking by a person with a bad knee.

Further, in the form of the second elastic string-like member 20 in the walking assistance device 1 being bifurcated between the position in the lower part of the thigh and the position in the upper part of the lower leg, the two lines of the second elastic string-like member 20 are bound together at a lower thigh binding part 20d being a position in a lower thigh part. Binding at the position of the lower thigh part provides a hamstring protective measure. The position of the lower thigh binding part 20d is preferably a position about ⅓ of the thigh from the lower end of the thigh in the vertical direction.

Furthermore, in the form of the second elastic string-like member 20 being bifurcated between the position of the lower part of the thigh and the position of the upper part of the lower leg, the two lines of the second elastic string-like member 20 are bound together at an upper lower-leg binding part 20e being a position in an upper lower-leg part. Binding at the position of the upper lower-leg part can improve a feeling of fit of the walking assistance device 1 to the leg L. The position of the upper lower-leg binding part 20e is preferably a position about ⅓ of the lower leg from the upper end of the lower leg in the vertical direction.

Embodiment 2

Figure 5:
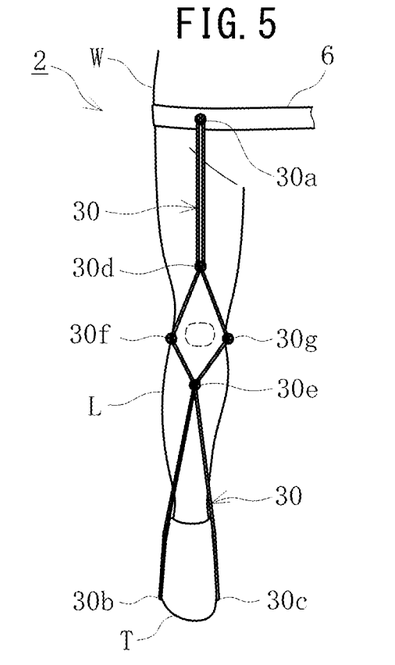
FIG. 5 is a diagram illustrating the front of a walking assistance device according to Embodiment 2 of the present disclosure.
Figure 6:
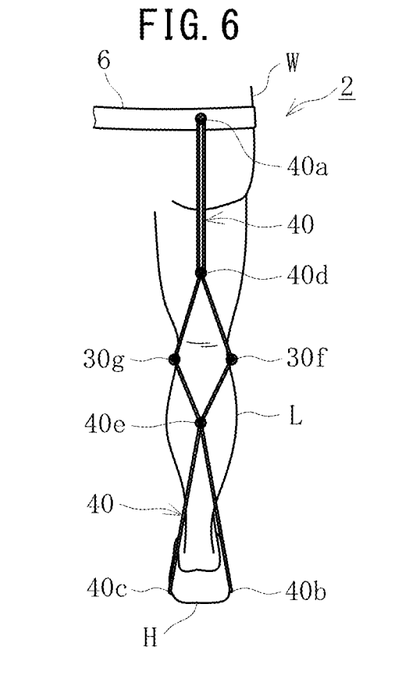
FIG. 6 is a diagram illustrating the rear of the walking assistance device according to Embodiment 2 of the present disclosure.
Figure 7:
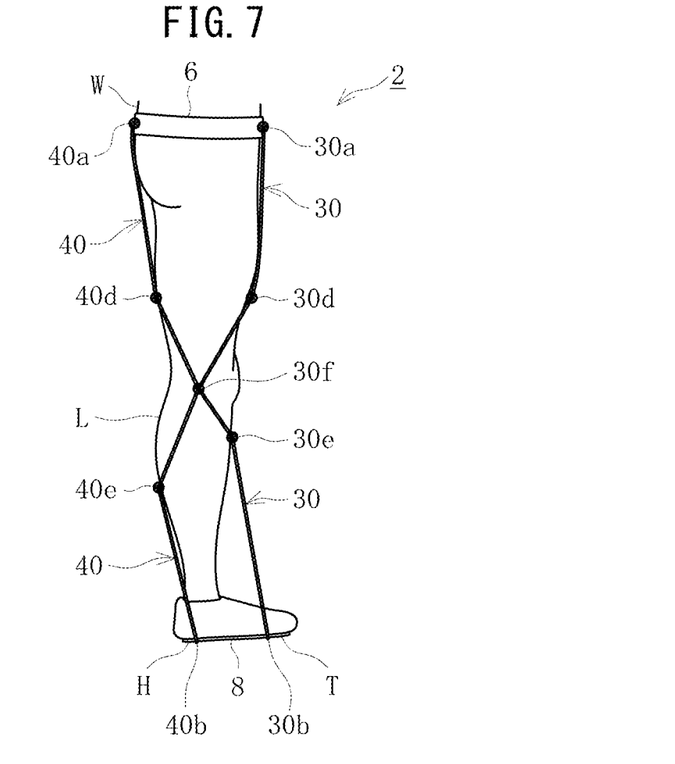
FIG. 7 is a diagram illustrating the left side of the walking assistance device according to Embodiment 2 of the present disclosure.
Figure 8:
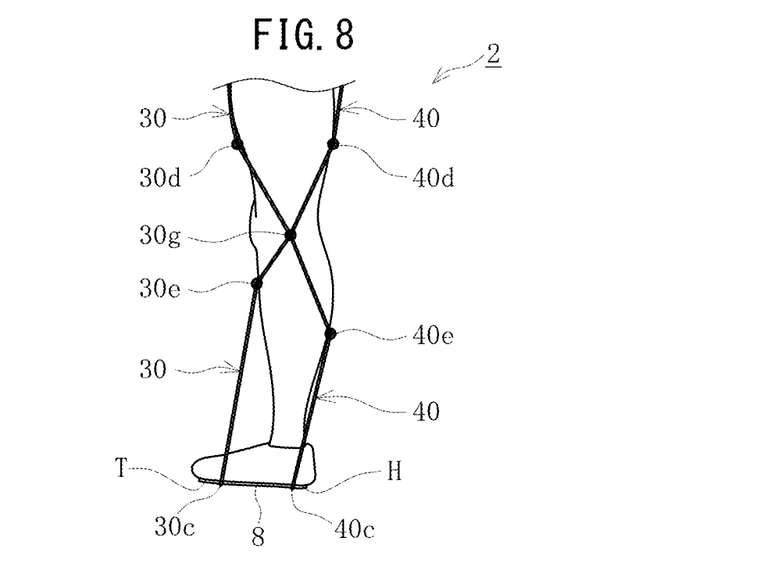
FIG. 8 is a diagram illustrating the right side of the walking assistance device according to Embodiment 2 of the present disclosure.

A walking assistance device according to Embodiment 2 will be described below by using FIG. 5 to FIG. 8. FIG. 5 is a diagram illustrating the front of the walking assistance device according to Embodiment 2 of the present disclosure. FIG. 6 is a diagram illustrating the rear of the walking assistance device according to Embodiment 2 of the present disclosure. FIG. 7 is a diagram illustrating the left side of the walking assistance device according to Embodiment 2 of the present disclosure. FIG. 8 is a diagram illustrating the right side of the walking assistance device according to Embodiment 2 of the present disclosure.

In a basic form of a first elastic string-like member 30 in the walking assistance device 2 according to the present embodiment, the first elastic string-like member 30 is bifurcated partway, a line of an upper part 30a is fixed to a lumbar region fixture 6 at the position of an anterior superior iliac spine, and a lower part extends in an instep direction of a leg L and is hooked to a toe region T of a sole. The first elastic string-like member 30 in the walking assistance device 2 may take a form of a single member being bifurcated partway, a form of doubling a single member and making part of the doubled member a single line by overlapping, or a form of two members being bound together partway and is not limited by the form of the member. The first elastic string-like member 30 will be described in the form of doubling a single member and making part of the doubled member a single line by overlapping in the following description.

Specifically, the upper part 30a of the first elastic string-like member 30 is fixed to the lumbar region fixture 6 at the position of the anterior superior iliac spine. Then, the first elastic string-like member 30 is bifurcated partway between a position above a kneecap and the position of a tibial tuberosity. Further, the first elastic string-like member 30 is bifurcated at the position of the tibial tuberosity, extends in a downward direction, enters the toe region T of the sole at an outer toe hooking part 30*b* being the outside of the toe region T of the sole, and passes through the toe region T of the sole from outside to inside. Then, the first elastic string-like member 30 passing through the toe region T of the sole from outside to inside extends from inside the toe region T of the sole in such a way as to fold back in an upward direction at an inner toe hooking part 30*c*.

Further, in a basic form of a second elastic string-like member 40 in the walking assistance device 2 according to the present embodiment, the second elastic string-like member 40 is bifurcated partway, an upper part of a line of an upper part 40*a* is fixed to the lumbar region fixture 6 above the position of the ischial tuberosity, and a lower part extends in an ankle direction of the leg L and is hooked to a heel region H of the sole. The second elastic string-like member 40 in the walking assistance device 2 may take a form of a single member being bifurcated partway, a form of doubling a single member and making part of the doubled member a single line by overlapping, or a form of two members being bound together partway and is not limited by the form of the member. The second elastic string-like member 40 will be described in the form of doubling a single member and making part of the doubled member a single line by overlapping in the following description.

Specifically, the upper part 40*a* of the second elastic string-like member 40 is fixed to the lumbar region fixture 6 above the position of the ischial tuberosity. Then, the second elastic string-like member 40 is bifurcated partway between a position in a lower part of a thigh and a position in an upper part of a lower leg. Further, the second elastic string-like member 40 is bifurcated at the position in the upper part of the lower leg, extends in the downward direction, enters the heel region H of the sole at an outer heel hooking part 40*b* being the outside of the heel region H of the sole, and passes through the heel region H of the sole from outside to inside. Then, the second elastic string-like member 40 passing through the heel region H of the sole from outside to inside extends from inside the heel region H of the sole in such a way as to fold back in the upward direction at an inner heel hooking part 40*c*.

While the first elastic string-like member 30 and the second elastic string-like member 40 may be directly stretched to the sole of the leg L, a thin-plate-shaped sole member 8 may be provided between the sole, and the first elastic string-like member 30 and the second elastic string-like member 40. Use of the sole member 8 can provide an effect of lifting the entire sole.

Further, in the walking assistance device 2, the first elastic string-like member 30 and the second elastic string-like member 40 bind the bifurcated parts of the first elastic string-like member 30 and the second elastic string-like member 40 together at an outer knee joint fissure gap binding part 30*f* being the position of an outer knee joint fissure gap and an inner knee joint fissure gap binding part 30*g* being the position of an inner knee joint fissure gap.

In the form of the first elastic string-like member 30 in the walking assistance device 2 being bifurcated between the position above the kneecap and the position of the tibial tuberosity, the two lines of the first elastic string-like member 30 are bound together at an upper kneecap binding part 30*d* being the position above the kneecap and a tibial tuberosity binding part 30*e* being the position of the tibial tuberosity. Binding at the position above the kneecap and the position of the tibial tuberosity further facilitates walking by a person with a bad knee.

Further, in the form of the second elastic string-like member 40 in the walking assistance device 2 being bifurcated between the position in the lower part of the thigh and the position in the upper part of the lower leg, the two lines of the second elastic string-like member 40 are bound together at a lower thigh binding part 40*d* being a position in a lower thigh part. Binding at the position of the lower thigh part provides a hamstring protective measure. The position of the lower thigh binding part 40*d* is preferably a position about ⅓ of the thigh from the lower end of the thigh in the vertical direction.

Furthermore, in the form of the second elastic string-like member 40 being bifurcated between the position in the lower part of the thigh and the position in the upper part of the lower leg, the two lines of the second elastic string-like member 40 are bound together at an upper lower-leg binding part 40*e* being a position in an upper lower-leg part. Binding at the position of the upper lower-leg part can improve a feeling of fit of the walking assistance device 2 to the leg L. The position of the upper lower-leg binding part 40*e* is preferably a position about ⅓ of the lower leg from the upper end of the lower leg in the vertical direction.

Embodiment 3

Figure 9:
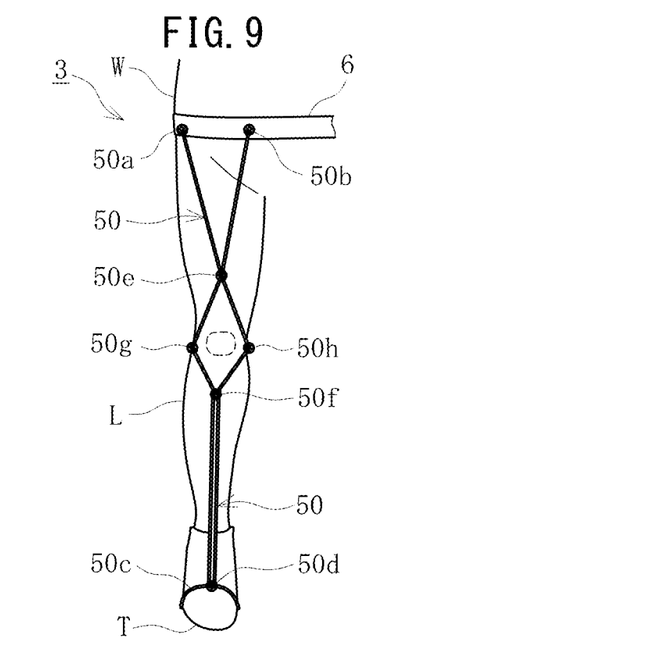
FIG. 9 is a diagram illustrating the front of a walking assistance device according to Embodiment 3 of the present disclosure.
Figure 10:
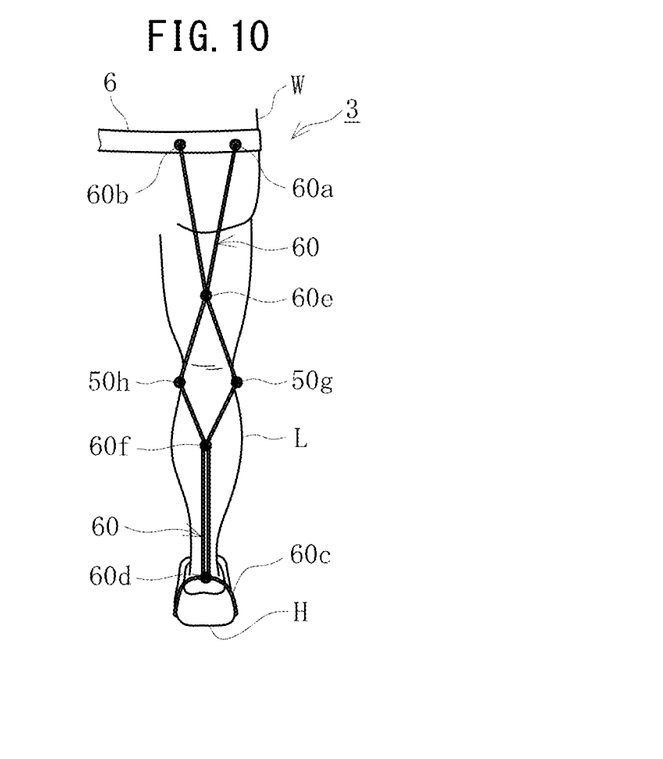
FIG. 10 is a diagram illustrating the rear of the walking assistance device according to Embodiment 3 of the present disclosure.
Figure 11:
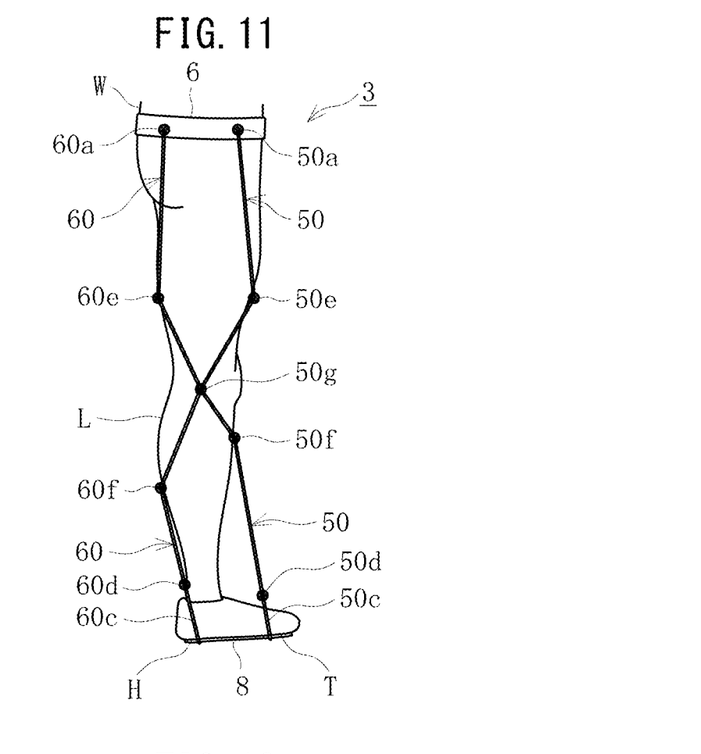
FIG. 11 is a diagram illustrating the left side of the walking assistance device according to Embodiment 3 of the present disclosure.
Figure 12:
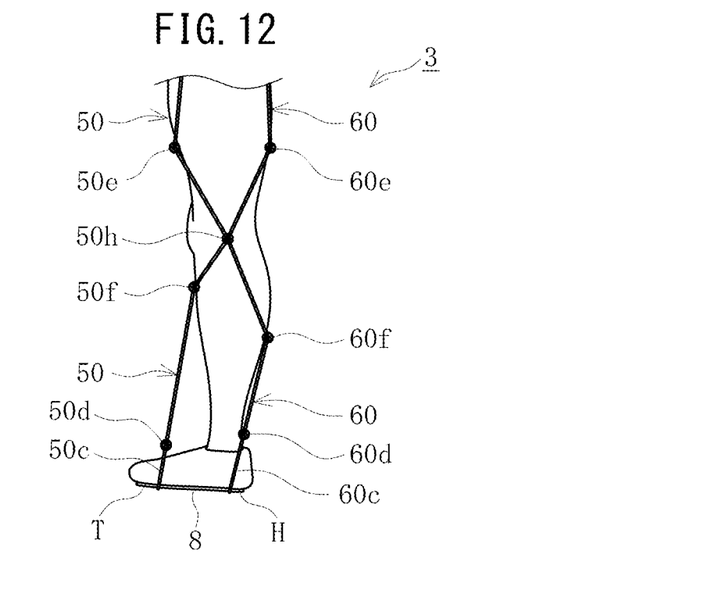
FIG. 12 is a diagram illustrating the right side of the walking assistance device according to Embodiment 3 of the present disclosure.

A walking assistance device according to Embodiment 3 will be described below by using FIG. 9 to FIG. 12. FIG. 9 is a diagram illustrating the front of the walking assistance device according to Embodiment 3 of the present disclosure. FIG. 10 is a diagram illustrating the rear of the walking assistance device according to Embodiment 3 of the present disclosure. FIG. 11 is a diagram illustrating the left side of the walking assistance device according to Embodiment 3 of the present disclosure. FIG. 12 is a diagram illustrating the right side of the walking assistance device according to Embodiment 3 of the present disclosure.

In a basic form of a first elastic string-like member 50 in the walking assistance device 3 according to the present embodiment, part of the first elastic string-like member 50 is bifurcated as two bifurcated upper parts 50*a* and 50*b*, the upper parts 50*a* and 50*b* are fixed to a lumbar region fixture 6 at positions with an anterior superior iliac spine in between, and a lower part 50*c* extends in an instep direction of a leg L and is hooked to a toe region T of a sole. The first elastic string-like member 50 in the walking assistance device 3 may take a form of an upper part of a single member being bifurcated, a form of doubling a single member and making part of the doubled member a single line by overlapping, or a form of two members being bound together partway and is not limited by the form of the member. The first elastic string-like member 50 is described in the form of doubling a single member and making part of the doubled member a single line by overlapping in the following description.

Specifically, the upper part 50*a* being one upper part of the first elastic string-like member 50 is fixed to the lumbar region fixture 6 at one of the positions with the anterior superior iliac spine in between, and the upper part 50*b* being the other upper part is fixed to the lumbar region fixture 6 at the other of the positions with the anterior superior iliac spine in between. Then, the bifurcated first elastic string-like member 50 is bound together as a single line partway to the lower part 50*c*, and the lower part 50*c* extending to the toe in a downward direction becomes annular at a lower part binding part 50*d* and is hooked to the toe region T of the sole of the leg L.

Further, in a basic form of a second elastic string-like member 60 in the walking assistance device 3 according to the present embodiment, part of the second elastic string-like member 60 is bifurcated as two bifurcated upper parts 60*a* and 60*b*, the upper parts 60*a* and 60*b* are fixed to the lumbar region fixture 6 above positions with an ischial tuberosity in between, and a lower part 60*c* extends in an ankle direction of the leg L and is hooked to a heel region H of the sole. The second elastic string-like member 60 in the walking assistance device 3 may take a form of an upper part of a single member being bifurcated, a form of doubling a single member and making part of the doubled member a single line by overlapping, or a form of two members being bound together partway and is not limited by the form of the member. The second elastic string-like member 60 will be described in the form of doubling a single member and making part of the doubled member a single line by overlapping in the following description.

Specifically, the upper part 60*a* being one upper part of the second elastic string-like member 60 is fixed to the lumbar region fixture 6 above one of the positions with the ischial tuberosity in between, and the upper part 60*b* being the other upper part is fixed to the lumbar region fixture 6 above the other of the positions with the ischial tuberosity in between. Then, the bifurcated second elastic string-like member 60 is bound together as one line partway to the lower part 60*c*, and the lower part 60*c* extending to the heel in the downward direction becomes annular at a lower part binding part 60*d* and is hooked to the heel region H of the sole of the leg L.

While the first elastic string-like member 50 and the second elastic string-like member 60 may be directly stretched to the sole of the leg L, a thin-plate-shaped sole member 8 may be provided between the sole, and the first elastic string-like member 50 and the second elastic string-like member 60. Use of the sole member 8 can provide an effect of lifting the entire sole.

Further, in the walking assistance device 3, each of the first elastic string-like member 50 and the second elastic string-like member 60 descends from the lumbar region fixture 6 in two lines, and the bifurcated parts of the first elastic string-like member 50 and the second elastic string-like member 60 are bound together at an outer knee joint fissure gap binding part 50*g* being the position of an outer knee joint fissure gap and an inner knee joint fissure gap binding part 50*h* being the position of an inner knee joint fissure gap.

In the walking assistance device 3, the bifurcated parts of the first elastic string-like member 50 extending in the vertical direction may be bound together at an upper kneecap binding part 50*e* being a position above a kneecap and a tibial tuberosity binding part 50*f* being the position of a tibial tuberosity in order to further facilitate walking by a person with a bad knee. As described above, the first elastic string-like member 50 extends in one line below the tibial tuberosity binding part 50*f*.

Furthermore, in the walking assistance device 4, the bifurcated parts of the second elastic string-like member 60 extending in the vertical direction may be bound together at a lower thigh binding part 60*e* being a position in a lower thigh part as a hamstring protective measure. The position of the lower thigh binding part 60*e* is preferably a position about ⅓ of the thigh from the lower end of the thigh in the vertical direction. Further, in order to improve a feeling of fit of the walking assistance device 3 to the leg L, the two lines of the second elastic string-like member 60 extending in the vertical direction may be bound together at an upper lower-leg binding part 60*f* being a position in an upper lower-leg part. The position of the upper lower-leg binding part 60*f* is preferably a position about ⅓ of the lower leg from the upper end of the lower leg in the vertical direction.

Embodiment 4

Figure 13:
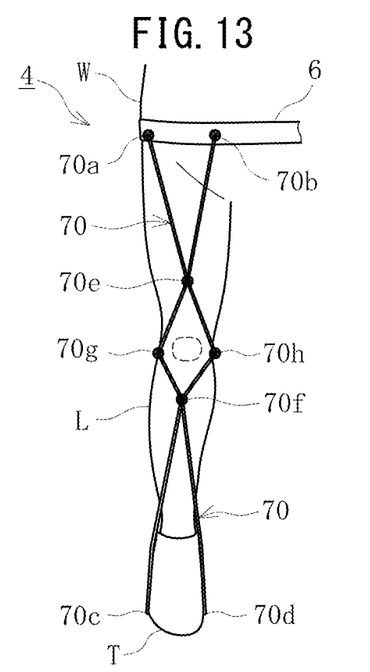
FIG. 13 is a diagram illustrating the front of a walking assistance device according to Embodiment 4 of the present disclosure.
Figure 14:
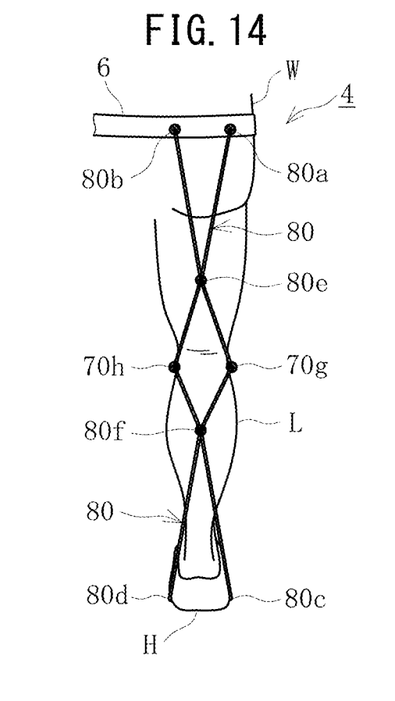
FIG. 14 is a diagram illustrating the rear of the walking assistance device according to Embodiment 4 of the present disclosure.
Figure 15:
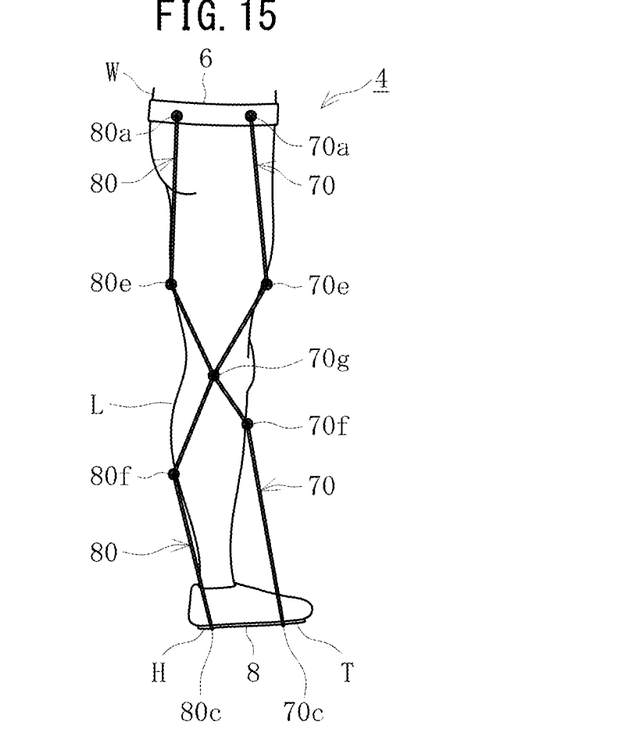
FIG. 15 is a diagram illustrating the left side of the walking assistance device according to Embodiment 4 of the present disclosure.
Figure 16:
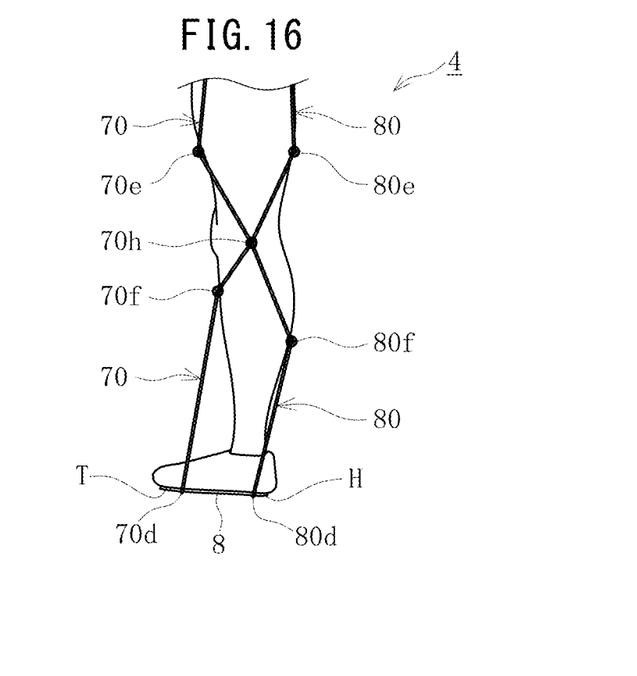
FIG. 16 is a diagram illustrating the right side of the walking assistance device according to Embodiment 4 of the present disclosure.

A walking assistance device according to Embodiment 4 will be described below by using FIG. 13 to FIG. 16. FIG. 13 is a diagram illustrating the front of the walking assistance device according to Embodiment 4 of the present disclosure. FIG. 14 is a diagram illustrating the rear of the walking assistance device according to Embodiment 4 of the present disclosure. FIG. 15 is a diagram illustrating the left side of the walking assistance device according to Embodiment 4 of the present disclosure. FIG. 16 is a diagram illustrating the right side of the walking assistance device according to Embodiment 4 of the present disclosure.

In a basic form of a first elastic string-like member 70 in the walking assistance device 4 according to the present embodiment, the first elastic string-like member 70 is doubled and includes two bifurcated upper parts 70*a* and 70*b*, and the upper parts 70*a* and 70*b* are fixed to a lumbar region fixture 6 at positions with an anterior superior iliac spine in between and are stretched to a toe region T of a sole of a leg L. The first elastic string-like member 70 in the walking assistance device 4 may take a form of doubling a single member into two lines or a form of using two members and is not limited by the form of the member. The first elastic string-like member 70 will be described in the form of doubling a single member into two lines in the following description.

Specifically, the upper part 70*a* being one upper part of the first elastic string-like member 70 is fixed to the lumbar region fixture 6 at one of the positions with the anterior superior iliac spine in between, extends in a downward direction, enters the toe region T of the sole at an outer toe hooking part 70*c* being the outside of the toe region T of the sole, and passes through the toe region T of the sole from outside to inside. Then, the first elastic string-like member 70 passing through the toe region T of the sole from outside to inside extends from inside the toe region T of the sole in such a way as to fold back in an upward direction at an inner toe hooking part 70*d*; and the upper part 70*b* being the other upper part is fixed to the lumbar region fixture 6 at another of the positions with the anterior superior iliac spine in between.

Further, in a basic form of a second elastic string-like member 80 in the walking assistance device 4 according to the present embodiment, the second elastic string-like member 80 is doubled and includes two bifurcated upper parts 80*a* and 80*b*, and the upper parts 80*a* and 80*b* are fixed to the lumbar region fixture 6 above positions with an ischial tuberosity in between and are stretched to a heel region H of the sole of the leg L. The second elastic string-like member 80 in the walking assistance device 4 may take a form of doubling a single member into two lines or a form of using two members and is not limited by the form of the member. The second elastic string-like member 80 will be described in the form of doubling a single member into two lines in the following description.

Specifically, the upper part 80*a* being one upper part of the second elastic string-like member 80 is fixed to the lumbar region fixture 6 above one of the positions with the ischial tuberosity in between, extends therefrom in the downward direction, enters a heel region H of the sole at an outer heel hooking part 80c being the outside of the heel region H of the sole, and passes through the heel region H of the sole from outside to inside. Then, the second elastic string-like member 80 passing through the heel region H of the sole from outside to inside extends from inside the heel region H of the sole in such a way as to fold back in the upward direction at an inner heel hooking part 80d; and the upper part 80b being the other upper part is fixed to the lumbar region fixture 6 above the other of the positions with the ischial tuberosity in between.

While the first elastic string-like member 70 and the second elastic string-like member 80 may be directly stretched to the sole of the leg L, a thin-plate-shaped sole member 8 may be provided between the sole, and the first elastic string-like member 70 and the second elastic string-like member 80. Use of the sole member 8 can provide an effect of lifting the entire sole.

Further, in the walking assistance device 4, the first elastic string-like member 70 and the second elastic string-like member 80 are bound together at an outer knee joint fissure gap binding part 70g being the position of an outer knee joint fissure gap and an inner knee joint fissure gap binding part 70h being the position of an inner knee joint fissure gap.

In the walking assistance device 4, the two lines of the first elastic string-like member 70 extending in the vertical direction may be bound together at an upper kneecap binding part 70e being a position above a kneecap and a tibial tuberosity binding part 70f being the position of a tibial tuberosity in order to further facilitate walking by a person with a bad knee.

Furthermore, in the walking assistance device 4, the two lines of the second elastic string-like member 80 extending in the vertical direction may be bound together at a lower thigh binding part 80e being a position in a lower thigh part as a hamstring protective measure. The position of the lower thigh binding part 80e is preferably a position about ⅓ of the thigh from the lower end of the thigh in the vertical direction. Further, in order to improve a feeling of fit of the walking assistance device 4 to the leg L, the two lines of the second elastic string-like member 80 extending in the vertical direction may be bound together at an upper lower-leg binding part 80f being a position in an upper lower-leg part. The position of the upper lower-leg binding part 80f is preferably a position about ⅓ of the lower leg from the upper end of the lower leg in the vertical direction.

Figure 17:
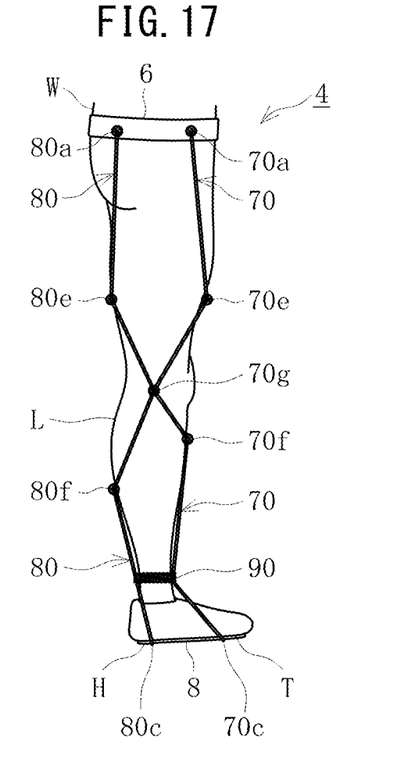
FIG. 17 is a diagram illustrating the left side of the walking assistance device according to Embodiment 4 of the present disclosure in another method of use.

For a person with an unstable ankle part, the first elastic string-like member 70 and the second elastic string-like member 80 may be fixed to an ankle by an ankle binding fixture 90 as illustrated in the diagram in FIG. 17 illustrating the left side of the walking assistance device according to Embodiment 4 of the present disclosure in another method of use.

For example, the ankle binding fixture 90 may be used in such a way that the first elastic string-like member 70 and the second elastic string-like member 80 are wound around and fixed to an ankle together by a velvet fastener. Further, the ankle binding fixture 90 does not need to be a single member; and the first elastic string-like member 70 may be fixed to an ankle by one ankle binding fixture, and the second elastic string-like member 80 may be fixed to the ankle by another ankle binding fixture. Thus, the ankle binding fixture 90 may take any form as long as the first elastic string-like member 70 and the second elastic string-like member 80 can be fixed to an ankle. Then, the ankle binding fixture 90 can be used in common among the walking assistance devices according to the present disclosure including the other embodiments.

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

INDUSTRIAL APPLICABILITY

As described above, the present disclosure can provide a walking assistance device that can provide support for facilitating walking while lifting the sole of a foot.

REFERENCE SIGNS LIST

1 Walking assistance device
2 Walking assistance device
3 Walking assistance device
4 Walking assistance device
6 Lumbar region fixture
8 Sole member
10 First elastic string-like member
10a Upper part
10b Lower part
10c Lower part binding part
10d Upper kneecap binding part
10e Tibial tuberosity binding part
10f Outer knee joint fissure gap binding part
10g Inner knee joint fissure gap binding part
20 Second elastic string-like member
20a Upper part
20b Lower part
20c Lower part binding part
20d Lower thigh binding part
20e Upper lower-leg binding part
30 First elastic string-like member
30a Upper part
30b Outer toe hooking part
30c Inner toe hooking part
30d Upper kneecap binding part
30e Tibial tuberosity binding part
30f Outer knee joint fissure gap binding part
30g Inner knee joint fissure gap binding part
40 Second elastic string-like member
40a Upper part
40b Outer heel hooking part
40c Inner heel hooking part
40d Lower thigh binding part
40e Upper lower-leg binding part
50 First elastic string-like member
50a Upper part
50b Upper part
50c Lower part
50d Lower part binding part
50e Upper kneecap binding part
50f Tibial tuberosity binding part
50g Outer knee joint fissure gap binding part
50h Inner knee joint fissure gap binding part
60 Second elastic string-like member
60a Upper part 60b Upper part
60c Lower part
60d Lower part binding part
60e Lower thigh binding part
60f Upper lower-leg binding part
70 First elastic string-like member
70a Upper part
70b Upper part
70c Outer toe hooking part
70d Inner toe hooking part
70e Upper kneecap binding part
70f Tibial tuberosity binding part
70g Outer knee joint fissure gap binding part
70h Inner knee joint fissure gap binding part
80 Second elastic string-like member
80a Upper part
80b Upper part
80c Outer heel hooking part
80d Inner heel hooking part
80e Lower thigh binding part
80f Upper lower-leg binding part
90 Ankle binding fixture

The invention claimed is:

1. A walking assistance device for assisting walking, the walking assistance device comprising:
   a belt-shaped lumbar region fixture configured to be wound around a lumbar region;
   a first elastic string-like member, an upper part of which is configured to be fixed to the lumbar region fixture at a position of an anterior superior iliac spine and a lower part of which extends in an instep direction and is configured to be hooked to a toe region of a sole; and
   a second elastic string-like member, an upper part of which is configured to be fixed to the lumbar region fixture above a position of an ischial tuberosity and a lower part of which extends in an ankle direction and is configured to be hooked to a heel region of the sole, wherein
   each of the first elastic string-like member and the second elastic string-like member is configured to be bifurcated near a knee of a leg, and
   the bifurcated parts of the first elastic string-like member and the second elastic string-like member are configured to be directly bound to each other at positions of an outer knee joint fissure gap and an inner knee joint fissure gap.

2. The walking assistance device according to claim 1, wherein the first elastic string-like member is configured to be bifurcated between a position above a kneecap and a position of a tibial tuberosity.

3. The walking assistance device according to claim 2, wherein the second elastic string-like member is configured to be bifurcated between a position in a lower part of a thigh and a position in an upper part of a lower leg.

4. The walking assistance device according to claim 2, wherein the first elastic string-like member and the second elastic string-like member are configured to be fixed to an ankle by an ankle binding fixture.

5. The walking assistance device according to claim 1, wherein the second elastic string-like member is configured to be bifurcated between a position in a lower part of a thigh and a position in an upper part of a lower leg.

6. The walking assistance device according to claim 5, wherein the first elastic string-like member and the second elastic string-like member are configured to be fixed to an ankle by an ankle binding fixture.

7. The walking assistance device according to claim 1, wherein the first elastic string-like member and the second elastic string-like member are configured to be fixed to an ankle by an ankle binding fixture.

8. A walking assistance device for assisting walking, the walking assistance device comprising:
   a belt-shaped lumbar region fixture configured to be wound around a lumbar region;
   a first elastic string-like member, an upper part of which is configured to be fixed to the lumbar region fixture at left and right positions with an anterior superior iliac spine in between and a lower part of which extends in an instep direction and is configured to be hooked to a toe region of a sole; and
   a second elastic string-like member, an upper part of which is configured to be fixed to the lumbar region fixture above left and right positions with an ischial tuberosity in between and a lower part of which extends in an ankle direction and is configured to be hooked to a heel region of the sole, for a right foot and/or a left foot, wherein
   each of the first elastic string-like member and the second elastic string-like member descends from a lumbar region fixture in two lines on one leg, and
   the bifurcated parts of the first elastic string-like member and the second elastic string-like member are configured to be directly bound to each other at positions of an outer knee joint fissure gap and an inner knee joint fissure gap.

9. The walking assistance device according to claim 8, wherein
   the first elastic string-like member descends from the lumbar region fixture in two lines, and
   the lines are configured to be bound together at a position above a kneecap and a position of a tibial tuberosity.

10. The walking assistance device according to claim 9, wherein
    the second elastic string-like member descends from the lumbar region fixture in two lines, and
    the lines are configured to be bound together at a position in a lower part of a thigh and a position in an upper part of a lower leg.

11. The walking assistance device according to claim 9, wherein the first elastic string-like member and the second elastic string-like member are configured to be fixed to an ankle by an ankle binding fixture.

12. The walking assistance device according to claim 8, wherein
    the second elastic string-like member descends from the lumbar region fixture in two lines, and
    the lines are configured to be bound together at a position in a lower part of a thigh and a position in an upper part of a lower leg.

13. The walking assistance device according to claim 12, wherein the first elastic string-like member and the second elastic string-like member are configured to be fixed to an ankle by an ankle binding fixture.

14. The walking assistance device according to claim 8, wherein the first elastic string-like member and the second elastic string-like member are configured to be fixed to an ankle by an ankle binding fixture.

* * * * *